United States Patent

Miyazaki et al.

[11] Patent Number: 5,540,935
[45] Date of Patent: Jul. 30, 1996

[54] REACTIVE VESICLE AND FUNCTIONAL SUBSTANCE-FIXED VESICLE

[75] Inventors: Tsuyoshi Miyazaki, Tsukuba; Kazuo Maruyama, Sagamihara; Motoharu Iwatsuru, Hachioji; Kouzoh Sanchika, Kawasaki; Mitsuhiro Nishida, Amagasaki; Tohru Yasukohchi, Kawasaki; Shigeru Kitano, Tsukuba; Akinori Suginaka, Chigasaki; Yoshihito Kadoma, Kobe, all of Japan

[73] Assignee: NOF Corporation, Tokyo, Japan

[21] Appl. No.: 349,362

[22] Filed: Dec. 5, 1994

[30] Foreign Application Priority Data

| Dec. 6, 1993 | [JP] | Japan | 5-305611 |
| Dec. 6, 1993 | [JP] | Japan | 5-305612 |
| Dec. 16, 1993 | [JP] | Japan | 5-317026 |
| Dec. 16, 1993 | [JP] | Japan | 5-317027 |
| Jun. 17, 1994 | [JP] | Japan | 6-135954 |

[51] Int. Cl.⁶ ................................. A61K 9/127
[52] U.S. Cl. ........................ 424/450; 428/402.2
[58] Field of Search ............. 424/450; 428/402.2

[56] References Cited

U.S. PATENT DOCUMENTS

| 5,190,822 | 3/1993 | Nishikawa et al. | 428/402.2 |
| 5,395,619 | 3/1995 | Zalipsky | 424/450 |
| 5,399,331 | 3/1995 | Loughrey | 424/450 |

FOREIGN PATENT DOCUMENTS

| 0526700 | 5/1992 | European Pat. Off. |
| 054384 | 3/1988 | Japan. |
| 90/04384 | 5/1990 | WIPO. |
| 91/16040 | 10/1991 | WIPO. |
| 94/22429 | 10/1994 | WIPO. |

OTHER PUBLICATIONS

Journal of Liposome Research, vol. 2, No. 3, 1992, pp. 321–334, New York.
Database WPI, Section Ch, Week 9423, Derwent Publications Ltd.; AN 94-188081 & JP-A-6 126 152 (Nippon Oils & Fats Co. Ltd.) 10 May 1994.

*Primary Examiner*—Gollamudi S. Kishore
*Attorney, Agent, or Firm*—Flynn, Thiel, Boutell & Tanis

[57] ABSTRACT

A reactive vesicle comprising, as a vesicle-forming component, a reactive phospholipid derivative represented by the following general formula (1) and a functional substance-fixed vesicle prepared by reacting the reactive vesicle with a functional substance:

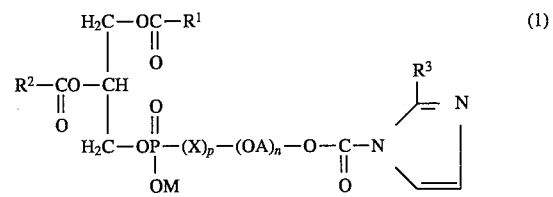

in which $R^1C(=O)$ and $R^2C(=O)$ each represent an aliphatic acyl group, $R^3$ denotes hydrogen atom or methyl group, OA represents an oxyalkylene group of 2–4 carbon atoms, n indicates the average number of moles of added oxyalkylene group and is 1–1,000, p is 0 or 1, X represents

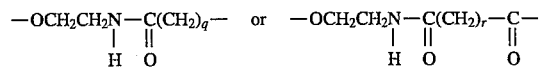

with q and r each being an integer of 0 to 4 or 1 to 4, respectively, and M denotes hydrogen atom or an alkli metal atom.

10 Claims, No Drawings

REACTIVE VESICLE AND FUNCTIONAL SUBSTANCE-FIXED VESICLE

FIELD OF THE INVENTION

The present invention relates to a reactive vesicle and to a functional substance-fixed vesicle. More specifically, the present invention relates to a reactive vesicle and a functional substance-fixed vesicle as well as a drug delivery vesicle prepared therefrom, especially one having a target-directing property, to be used as various functional liposomes and fatty emulsions, such as a drug carrier for medicaments etc., testing drugs, diagnostic drugs, sensors, fixed catalysts, bioreactors, bioelectronics elements and a substitute for microcapsules.

BACKGROUND OF THE INVENTION

A liposome is a lipid vesicle composed of a phospholipid bilayer it has been attempted to find its applications in various fields. Attention has been paid, in particular, to its application as a drug carrier and sensors for diagnosis and detection, where large problems have been encountered in providing the liposome with a specific function by fixing a special functional substance onto or into the liposome and in maintaining the concentration of liposome cells in the blood.

Heretofore, there have been reported as for the fixation of functional substances onto or into a liposome, for example, a method in which fragments of an antibody are bound to an aminoethyl carbamoyl-methyl group substituted in a polysaccharide on the surface of a liposome covered with a pullulan derivative via γ-maleimidobutyloxysuccinimidyl, "Biochem. Biophys. Acta.", 898, 323 (1987), and a method in which an antibody is fixed onto a liposome in such a manner that a glycolipid is added preliminarily to the ingredients for forming the liposome membrane and, after the liposome has been formed, a periodate oxidation is carried out and the thereby formed aldehyde group is reacted with the antibody. "J. Biol. Chem.", 255, 10509 (1980).

These prior arts include, however, a problem that a multistep chemical reaction on the liposome membrane has to be incorporated after the liposome has been formed and, thus, the amount of the contemplated functional substance introduced is limited to a lower value, with the simultaneous high possibility of contamination by the by-products and impurities, bringing about a large probability of damage of the liposome membrane.

On the other hand, it has been pointed out that no sufficient effect is achieved by the use of a liposome, since a large part of the liposome is caught by organs in the reticuloendothelial system, such as the liver, spleen etc., upon administration of the liposome product [Cancer Res., 43, 5328 (1983)]. In order to solve problems by the above-mentioned liposome capture in the organs of the reticuloendothelial system and by the low stability of the liposome itself, such as the tendency to collapse and coagulation, an attempt has been made to introduce polyethylene glycol chains into the surface layer of a liposome. WO 90/4384, Japanese Patent Application Kokai No. 249717/1989 and FEBS Letters, 268, 235 (1990). Also, it has been made clear that a liposome modified by polyethylene glycol can afford to maintain the liposome concentration in blood for long period of time. Biochem. Biophys. Acta, 1066, 29–36 (1991).

However, the liposome having introduced therein polyethylene glycol chains does not react with functional substances, so that these functional substances can not be fixed on the liposome surface.

In European Patent Publication No. 526700, it is taught that an antibody-bound liposome containing a drug in which the problem of drug capturing in organs of the reticuloendothelial system is improved can be obtained by reacting a maleimide group-containing liposome first with a protein provided with thiol groups (thiolated protein) and reacting, then, the remaining maleimide groups with a compound having a moiety of a polyalkylene glycol having thiol groups (thiolated polyalkylene glycol).

This liposome has, however, a defect that the expected effect is not attained sufficiently, since the antibody is hidden behind the polyalkylene glycol layer and the reaction of the antibody with the target site is obstructed.

In WO 91/16040, a liposome preparation is disclosed, which comprises an anionic group-containing polyethylene glycol derivative, such as an a α-stearyl-ω-propionic acid-polyoxyethylene. However, this polyoxyethylene derivative tends to separate off easily from the liposome membrane, since the hydrophobic moiety thereof consists of a monoalkyl group, so that a liposome containing such a polyoxyethylene derivative as the membrane-forming component is inferior in long term stability.

SUMMARY OF THE INVENTION

An object of the present invention is to solve the problems of the prior arts explained above by providing a reactive vesicle in which (poly)oxyalkylene chains having provided at the top end thereof with a reactive oxycarbonylimidazole group are introduced and which permits various functional substances to be fixed easily and efficiently in a larger amount by a covalent bond onto the top ends of the (poly)oxyalkylene chains and which is superior in long term storge stability.

Another object of the present invention is to provide a functional substance-fixed vesicle which comprises a vesicle having combined on its surface, through an intermediary spacer consisting of a (poly)oxyalkylene chain, a functional substance and which is superior in long term storge stability and is capable of maintaining its concentration in blood for long periods of time, while revealing sufficient functionality of the functional substance fixed thereon.

A further object of the present invention is to provide a drug delivery vesicle made from the reactive vesicle or made of the functional substance-fixed vesicle, especially one having a target-directing property.

According to the present invention, there is provided a reactive vesicle, which comprises a vesicle containing a reactive phospholipid derivative represented by the following general formula (1):

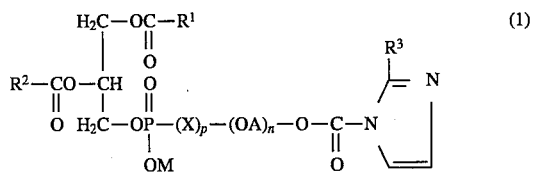

in which
$R^1C(=O)$ and $R^2C(=O)$ each represent an aliphatic acyl group having 3–30 carbon atoms and may be identical or different from each other,
$R^3$ denotes hydrogen atom or methyl group,
OA represents an oxyalkylene group of 2–4 carbon atoms,
n denotes the average addition mole number of added oxyalkylene group and is a positive number of 1–1,000, with the proviso that the oxyalkylene groups may be identical or different from each other and may be added randomly or in a block when n is 2 or higher, p is 0 or 1, X represents the group

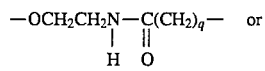

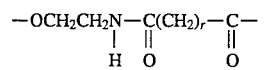

wherein q is an integer of 0 to 4 and r is an integer of 1 to 4 and

M denotes hydrogen atom or an alkali metal atom.

According to the present invention, there is provided also a functional substance-fixed vesicle comprising, as a vesicle-forming component, one or more phospholipid derivatives represented by the general formula (2):

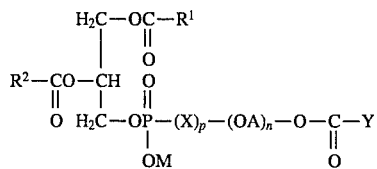

in which $R^1C(=O)$ and $R^2C(=O)$ each represent an aliphatic acyl group having 3–30 carbon atoms and may be identical or different from each other, OA represents an oxyalkylene group of 2–4 carbon atoms, n indicates the average addition mole number of added oxyalkylene group and is a positive number of 1–1,000, with the proviso that the oxyalkylene groups may be identical or different from each other and may be added randomly or in a block when n is 2 or higher, p is 0 or 1, X represents the group

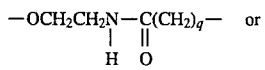

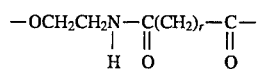

wherein q is an integer of 0 to 4 and r is an integer of 1 to 4,

M denotes hydrogen atom or an alkali metal atom and

Y denotes the residue of a functional substance.

According to the present invention, there is further provided a drug delivery vesicle, which comprises the reactive vesicle or the functional substance-fixed vesicle mentioned above.

DETAILED DESCRIPTION OF THE INVENTION

In the context of the present application, the term "(poly)oxyalkylene" does mean oxyalkylene or polyoxyalkylene. Similarly, the term "(poly)alkylene" means alkylene or polyalkylene.

The "vesicle" as used in the present invention means a cellular particle having a structure in which the hydrophilic groups of the phospholipid derivative represented by the general formula (1) or (2) and of other vesicle-forming components are oriented towards the aqueous phase from the surface membrane. Concrete examples thereof include a closed vesicle composed of a liposome, a fatty emulsion in which a mixture of vegetable oil and phospholipid is emulsified and micells.

The acyl groups of fatty acids represented by $R^1C(=O)$ and $R^2C(=O)$ in the general formula (1) or (2) are those having 3–30, preferably 8–20 carbon atoms inclusive of the carbonyl carbon. Specific examples of such acyl groups include those of saturated fatty acids, such as propionic acid, butyric acid, caproic acid, caprylic acid, pelargonic acid, capric acid, undecanoic acid, lauric acid, myristic acid, palmitic acid, stearic acid, arachic acid, behenic acid, lignoceric acid, solocic acid, montanic acid, melissic acid, 2-ethyl hexanoic acid; those of unsaturated fatty acids, such as oleic acid, linoleic acid, linolenic acid, erucic acid and 2,4-octadecadienoic acid; those of branched fatty acids, such as isostearic acid; and those of fatty acids having hydroxyl group in the alkyl moiety, such as ricinoleic acid and 12-hydroxy stearic acid.

In the reactive vesicle, the functional substance-fixed vesicle and the drug transporting vesicle according to the present invention, the acyl groups of fatty acids represented by $R^1C(=O)$ and $R^2C(=O)$ in the general formula (1) or (2) may preferably be those of myristic acid, palmitic acid, stearic acid, oleic acid and 2,4-octadecadienoic acid, in particular, palmitic acid, stearic acid and oleic acid, since these can produce a stable liposome or fatty emulsion. The groups $R^1C(=O)$ and $R^2C(=O)$ may either be identical with or different from each other.

The oxyalkylene group represented by OA in the general formula (1) or (2) has 2–4 carbon atoms, namely, for example, oxyethylene, oxypropylene, oxytrimethylene, oxy-1-ethyl-ethylene, oxy-1,2-dimethylethylene and oxytetramethylene. These oxyalkylene groups are derived from the addition of alkylene oxides, such as ethylene oxide, propylene oxide, oxetane, 1-butene oxide, 2-butene oxide and tetrahydrofuran.

The number n in the general formula (1) or (2) may be a positive number of 1–1,000, preferably, 10–300 and most preferably 20–120.

In case n is 2 or higher, the oxyalkylene groups in the phospholipid derivative may either be identical with or different from each other. If they are different, they may be in the form of random addition or block addition.

For providing the phospholipid derivative with hydrophilicity, the group OA may preferably be derived from a sole polyaddition of ethylene oxide, wherein n may preferably be 10 or higher. In case the polyoxyalkylene group is derived from the polyaddition of different alkylene oxides, it may preferably be composed of 20 mole % or more, preferably 50 mole % or more of oxyethylene groups. For providing the (poly)oxyalkylene chain with an oleophilicity, the number of moles of added alkylene oxide other than ethylene oxide is increased.

In the general formula (1) or (2), p denotes 0 or 1 and, if p=1, X is selected from the bivalent organic groups mentioned above.

$R^3$ of the general formula (1) represents a hydrogen atom or a methyl group. M of the general formula (1) or (2) denotes a hydrogen atom or an alkali metal atom, such as sodium or potassium.

In case p of the general formula (1) is 1, the reactive phospholipid derivative is represented by the general formula (1-1) or (1-2) given below and, if p is zero, it is represented by the general formula (1-3) also given below:

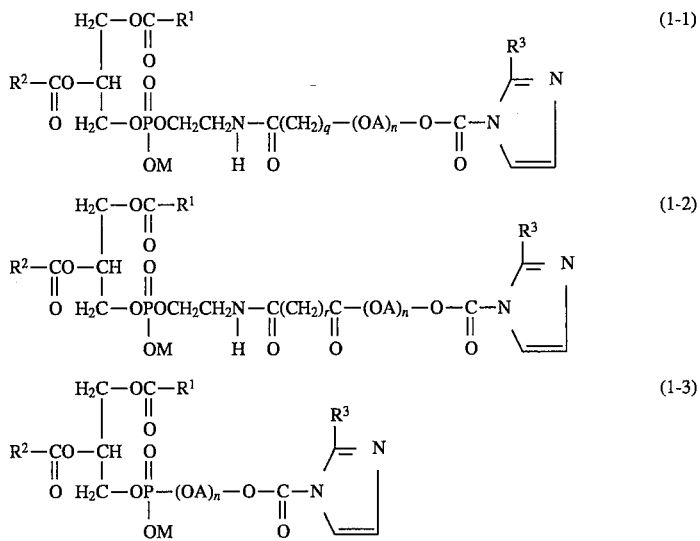

In these general formulae, the symbols which are the same as those of general formula (1) have the same meanings.

The reactive phospholipid derivative of general formula (1-1), namely that of general formula (1) with p=1, can be produced easily by, for example, reacting a (poly)oxyalkylene derivative having a carboxyl group at its one end and a hydroxyl group at the other end with N,N'-dicyclohexylcarbodiimide (DCC) to form an active derivative and subjecting this derivative then to a reaction with a phosphatidylethanolamine, whereupon the resulting product is reacted with N,N'-carbonyldiimidazole (CDI). The production procedures using an α-hydro-ω-carboxy polyoxyethylene, i.e., α-(2-carboxy)ethyl-ω-hydroxy polyoxyethylene, for the (poly)oxyalkylene derivative and dipalmitoyl-glycero-phosphoethanolamine (DPPEA) for the phosphatidylethanolamine is given in the following reaction scheme (3a):

The phospholipid derivatives can also be produced easily in an alternative way, for example, by preparing an active product of the (poly)oxyalkylene derivative by converting its carboxyl group into an acid chloride group using, for example, thionyl chloride or isobutyl chloroformate, or into an active ester using, for example, succinimide or N,N'-carbonyldiimidazole, and reacting this active product with a phosphatidylethanolamine, whereupon the resulting product is reacted with CDI. By this, phospholipid derivatives of general formula (1-1) with q=1 to 4 are obtained.

The phospholipid derivatives can be produced easily in a further alternative way by reacting a phosphatidylethanolamine with a (poly)oxyalkylene derivative having at each of its ends an oxycarbonyl imidazole group in a mixing mole proportion of 1:1 to 1:1,000. By this, phospholipid derivatives of the general formula (1-1) with q=0 are obtained.

(3a)

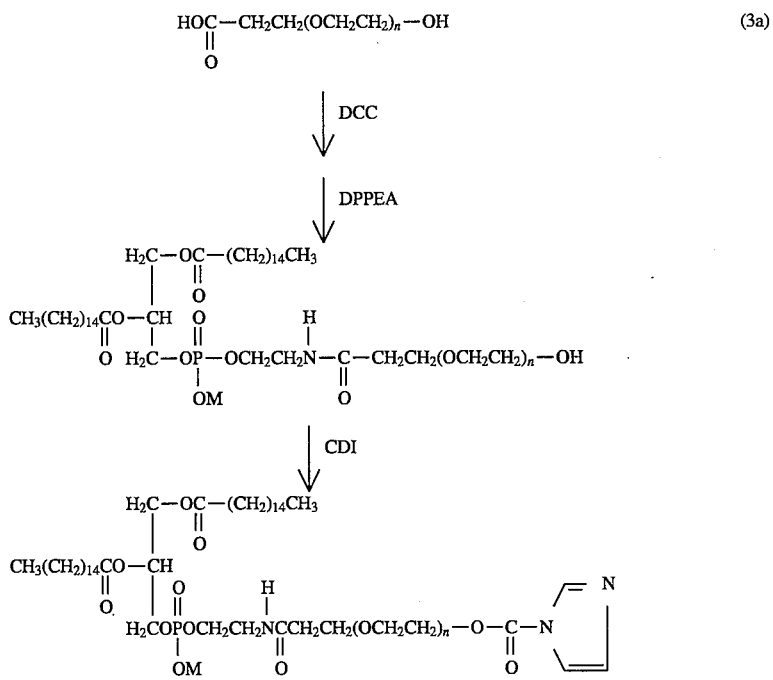

The above reactions can be realized without a solvent or in an aqueous medium, such as water, saline, a phosphate buffer, a tris buffer, a carbonate buffer or a borate buffer, or further in an organic solvent, such as toluene, acetonitrile, methanol, ethanol, 1,4-dioxane, tetrahydrofuran, chloroform, methylene chloride or diethyl ether, in atmospheric air or under an inert atmosphere of argon, helium or carbon dioxide gas at a temperature of $-40°$ to $+120°$ C., preferably $0°$ to $60°$ C., for 10 minutes to 240 hours, preferably 1–48 hours, preferably with agitation.

The phospholipid derivatives represented by the general formula (1) with $p=1$, namely, those of the general formula (1-2), can be produced easily, for example, in such a manner, that an $\alpha$-hydro-$\omega$-hydroxy polyoxyethylene is reacted with a dicarboxylic acid anhydride, such as succinic anhydride (SAN), in a mole proportion of 1:1 to 1:0.01, followed by purification by, for example, treatment in a column, to obtain a polyoxyethylene derivative having a carboxyl group at one end and a hydroxyl group at the other end, whereupon this polyoxyethylene derivative is reacted with a phosphatidylethanolamine in a similar manner as in the production of the phospholipid derivative of the general formula (1-1). The reaction sequence for this is shown in the following reaction scheme (3b), in which M and n have the same meanings as those given previously.

In the first step reaction, a phosphatidyl (poly)alkylene glycol is synthesized by reacting a phospholipid with an $\alpha$-hydro-$\omega$-hydroxy (poly)oxyalkylene in the presence of an enzyme phospholipase D (PLase-D). As the phspholipase D to be used here, either a commercial product or an extracted and purified product obtained by the method described in J. Biol. Chem., 242, 477–484 (1967) can be employed. As the phospholipid, for example, phosphatidylethanolamine, phosphatidylcholine, phosphatidylserine, phosphatidylinositol, phosphatidylglycerol or phosphatidic acid, can be employed. Phospholipase D may preferably be used in an amount of, though not limited specifically, 100 to 500 units per gram of the phospholipid. The mixing proportion of the phospholipid and the $\alpha$-hydro-$\omega$-hydroxy (poly)oxyalkylene may preferably be 5–100 moles of the $\alpha$-hydro-$\omega$-hydroxy (poly)oxyalkylene per mole of the phospholipid.

The reaction may be carried out preferably in an aqueous medium, such as an acetate buffer or a carbonate buffer, or in a mixed medium composed of such an aqueous medium and an organic solvent, such as chloroform, benzene, toluene, tetrahydrofuran or acetonitrile. The reaction may be effected at a temperature of $0°$–$80°$ C., preferably $30°$–$40°$ C., for 10 minutes–170 hours, preferably for 30 minutes to 24 hours.

The phosphatidyl (poly)alkylene glycol product obtained in this manner may be used for the second step reaction as

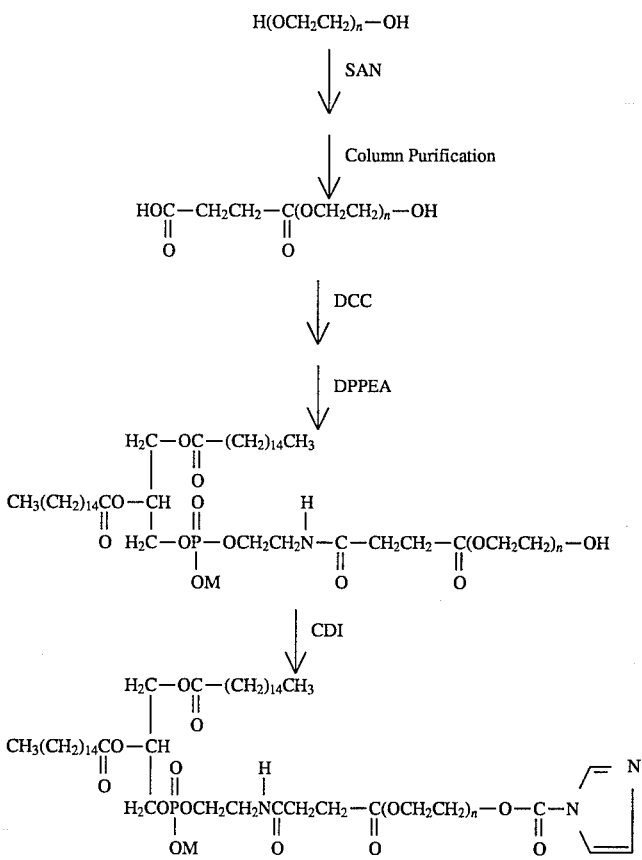

(3b)

The reactive phospholipid derivatives represented by the general formula (1) with $p=0$, namely those of the general formula (1-3), can be produced easily, for example, by a two-step reaction in the following way:

such or after isolation and purification by, for example, re-precipitation, treatment in a column, treatment by adsorption, ion-exchange, gel filtration, ultrafiltration or dyalysis.

In the second step reaction, the contemplated reactive phospholipid derivative is synthesized by reacting the phosphatidyl (poly)alkylene glycol with N,N'-carbonyldiimidazole or a substituted product thereof. While there is no special limitation in the mixing proportion of the starting reactants, it is preferable to use 0.1–100 moles, preferably 1–10 moles of N,N'-carbonyldiimidazole or its substitution product per mole of the phosphatidyl (poly)alkylene glycol.

The reaction may preferably be carried out in an organic solvent, such as chloroform, benzene, toluene, tetrahydrofuran or acetonitrile. The rection temperature may preferably be in the range from −100° C. to +100° C., preferably from 0° C. to 40° C., and the reaction duration may be in the range from 1 minute to 48 hours, preferably from 10 minutes to 6 hours.

The reaction course using an α-hydro-ω-hydroxy polyoxyethylene as the α-hydro-ω-hydroxy (poly) oxyalkylene is given in the following reaction scheme (4), in which $R^1C(=O)$, $R^2C(=O)$, M and n are the same as in the general formulae given above and PL-PEG represents phosphatidyl (poly)ethylene glycol:

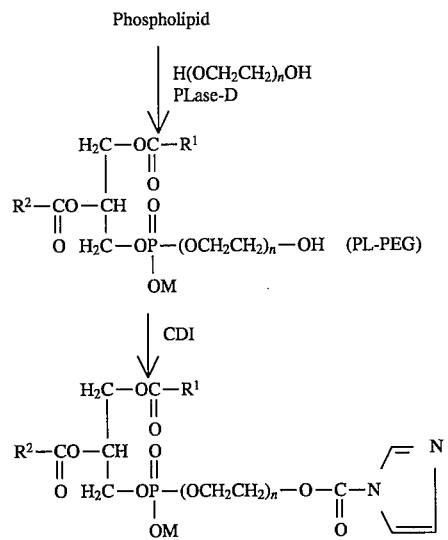

(4)

After the reactive phospholipid derivative represented by the general formula (1) has been produced as above, it can be used, for example, as a component for forming a vesicle, in the form of the reaction mixture as such or after it is isolated and purified from the reaction mixture by distillation, recrystallization, re-precipitation, treatment by adsorption, treatment in a column, gel filtration, ultrafiltration, dialysis, ion-exchange or thin layer chromatography.

The reactive vesicle according to the present invention comprises, as the vesicle-forming component, a reactive phospholipid derivative represented by the general formula (1). Since the reactive phospholipid derivtive to serve as the vesicle-forming component includes an oxycarbonylimidazole group which has a high reactivity to various functional substances having functional group(s) of amino, hydroxyl, thiol and so on, especially a primary amino group, a vesicle containing such a reactive phospholipid derivative will react easily with such functional substances. The reactive phospholipid derivative represented by the general formula (1) may be incorporated either solely or in combination of two or more of them. As the vesicle-forming component, other ones such as those which are capable of forming vesicles may be employed in addition to that represented by the general formula (1).

As other vesicle-forming components, for example, other phospholipids, such as soybean lecithin and yolk lecithin, cholesterol, Intralipid (Trademark, Otsuka Pharmaceuticl Co., Ltd.), soybean oil and safflower oil, may be employed. The reactive vesicle according to the present invention can be produced using these components by known methods.

Various functional substances can be introduced into the reactive vesicle obtained by using the reactive phospholipid derivative according to the present invention, by a covalent bond by making use of the oxycarbonylimidazole group or its substituted group in the compound represented by the general formula (1) as a functional group.

The functional substance-fixed vesicle according to the present invention contains the phospholipid derivative represented by the general formula (2) as a vesicle-forming component. Such a functional substance-fixed vesicle can be obtained by reacting the reactive vesicle with a functional substance having functional group(s) capable of reacting with an oxycarbonylimidazole group or a substituted group thereof.

The drug delivery vesicle according to the present invention comprises the reactive vesicle or the functional substance-fixed vesicle containing enclosed therein a drug, such as a medicament. In particular, if the functional substance fixed to the drug delivery vesicle composed of the functional substance-fixed vesicle is an antigen or an antibody, the resulting drug delivery vesicle possesses a target-directing property due to the action of the so-fixed antigen or antibody.

Below, the reactive vesicle, the functional substance-fixed vesicle and the drug delivery vesicle according to the present invention will be described in detail for each of their forms of liposomes, fatty emulsions and micells.

A reactive liposome as a representative reactive vesicle comprises the reactive phospholipid derivative represented by the general formula (1) as a membrane-forming component (vesicle-forming component). The content of the reactive phospholipid derivative represented by the general formula (1) may preferably be in the range of 0.01–50 mole %, preferably 0.5–30 mole %, based on the total moles of the reactive phospholipid derivative represented by the general formula (1) and other membrane-forming components. If this content is less than 0.01 mole %, the expected effect will be low and, if it exceeds 50 mole %, the stability of the liposome decreases and such a content is not chosen in general. The reactive phospholipid derivatives represented by the general formula (1) may each be used solely or in combination of two or more of them.

As other membrane-forming components to be used in combination with the reactive phospholipid derivative represented by the general formula (1), those which have hitherto found their application as the membrane-forming component of liposomes can be employed without limitation. Concrete examples thereof include phospholipids and polymerizable phospholipids having unsaturated group(s) in the acyl group of fatty acids, such as diphosphatidylglycerol, cardiolipin, phosphatidylinositol, phosphatidylserine, phosphatidylethanolamine, soybean lecithin, yolk lecithin, phosphatidylcholine and phosphatidylglycerol; glycolipids, such as sulfoxyribosyldiglyceride, digalactosyldiglyceride and lactosyldiglyceride; nonpolar lipids, such as cholesterols; and others, such as nonionic surfactants, phosphatidyl polyethylene glycol and reaction products of phosphatidylethanolamine with α-hydro-ω-hydroxy polyoxyethylene, such as those described in Biochem. Biophys. Acta, 1066, 29–36 (1991), as well as mixtures of them.

Reactive liposomes according to the present invention can be produced by various methods, for example, by dissolving a reactive phospholipid derivative represented by the general formula (1) and, if necessary, other membrane-forming components, such as other phospholipids such as lecithin, or cholesterols, in an adequate medium, such as an organic solvent, and processing the resulting solution into a liposome by a known technique, such as the extrusion method, vortex mixer method, ultrasonification method, surfactant-removal method, reversed phase evaporation, ethanol introducing method, prevesicle method, french-press method, W/O/W-emulsion method, annealing method or freeze-thawing method. By choosing an appropriate technique among them, reactive liposomes having various sizes and morphologies can be produced.

The reactive liposome obtained above has an oxycarbonylimidazole group, or its substituted group, suspended from both side surfaces of the resulting liposome membrane through an intermediary spacer consisting of a (poly)oxyalkylene chain, so that it can afford to fix various functional substances having functional group(s), such as amino, hydroxyl, thiol and the like, in particular, a primary amino group, easily and efficiently onto the bimolecular membrane of the liposome through a chemical bond, such as an urethane bond, carbonate bond, thiocarbonate bond or the like, through an intermediary spacer consisting of a (poly)oxyalkylene chain. In this manner, a functional substance-fixed liposome in which a functional substance is fixed on the liposome membrane through an intermediary (poly)oxyalkylene chain is obtained.

As the functional substances to be fixed onto the liposome membrane, various substances having, or provided by introduction with, functional groups such as those mentioned above, namely, amino, hydroxyl, thiol and so on, may be enumerated. Among them, those having or provided by introduction with primary amino groups are preferred. Specific examples thereof include labelling compounds, such as pigments, dyestuffs, radioactive labelling compounds, fluorescent compounds, chemiluminescent compounds and electrode-sensitive compounds; external stimulation-responsive compounds, such as light-responsive compounds, pH-responsive compounds and heat-responsive compounds; physiological substances, such as proteins including enzymes and antibodies, sugars, lipids, glycoproteins, glycolipids and hormones; and various medicaments.

As the antibody, those which are reactive with the epitopes existing specifically in the cells or tissue at the diseased site, such as polyclonal and monoclonal antibodies and partial units of them can be used. They may be of any origin, such as human, caprine, sheep, rabbit and chicken, and of any hybridoma. As the antigen, every substance capable of serving as an antigen to an antobody existing at the diseased site may be employed without limitation. For example, proteins, oligosaccharides, high molecular weight sugars, low molecular weight haptens and cholesterols may be enumerated. Here, a low molecular weight hapten should have either one of the functional groups among amino, hydroxyl and thiol in the molecule for fixation. By fixing such an antibody or antigen on the liposome, a target-directing property can be imparted to the liposome.

The functional substance-fixed liposomal vesicle according to the present invention comprises the phospholipid derivative represented by the general formula (2) as a membrane-forming component and can be obtained by reacting the reactive liposome with the functional substance. Thus, an oxycarbonylimidazole group, or substituted group thereof, present on the outer face of the reactive liposome will react with the functional group in the functional substance, such as amino, hydroxyl or thiol, to build a covalent bond of, for example, an urethane bond, carbonate bond or thiocarbonate bond, whereby the functional substance is fixed firmly on the liposome surface. In the general formula (2), the symbol Y represents the residue of the functional substance bound to the vesicle.

The reaction to fix the functional substance onto the reactive liposome membrane can be realized easily in various ways including a one-step technique, which comprises subjecting the reactive liposome and the functional substance to a reaction with each other in an adequate reaction medium, such as an aqueous medium, for example, physiological saline, phosphate buffer, carbonate buffer, tris buffer, acetate buffer or borate buffer, or further, a mixture of these aqueous mediums with an organic solvent, such as methanol, ethanol, acetone, acetonitrile, tetrahydrofuran, 1,4-dioxane, dimethylformamide, dimethylacetamide, dimethylsulfoxide and pyrrolidone, at a temperature from $-10°$ to $+120°$ C. and, in the case of reaction with an amino group, at a temperature, preferably, from $0°$ to $60°$ C., in particular, from $0°$ to $40°$ C., and, in the case of reaction with a hydroxyl or a thiol group, at a temperature, preferably, from $40°$ to $120°$ C., for a reaction period in the range from 5 minutes to 1,000 hours, preferably from 30 minutes to 72 hours, under agitation. For fixing a protein such as an antigen or an antibody, it is preferable to use an aqueous reaction medium with a pH of 4 to 12, preferably 6 to 10, at a temperature of $-10°$ to $+100°$ C. For the fixation reaction with an amino group, a temperature preferably of $0°$ to $60°$ C., and more preferably $0°$ to $40°$ C. may be chosen. In the case of a reaction with a hydroxyl or a thiol group, a reaction temperature of $50°$ to $80°$ C. and a reaction duration from 30 minutes to 200 hours, preferably from 1 minute to 48 hours are preferred. Reaction conditions other than those given above are undesirable, since the stability of the liposome will become lower. These reactions are carried out preferably under agitation A reaction sequence of the fixation of a functional substance having an amino, hydroxyl or thiol group with the liposome membrane may be explained schematically by the following reaction schemes (5a) to (5c) in which $R^3$, OA and n are the same as explained previously, Lip indicates the liposome and Z has the meaning as explained by these formulae, wherein $H_2N$-Z, HO-Z and HS-Z each indicate the functional substance and -HN-Z, -O-Z and -S-Z each corresponds to Y of the general formula (2):

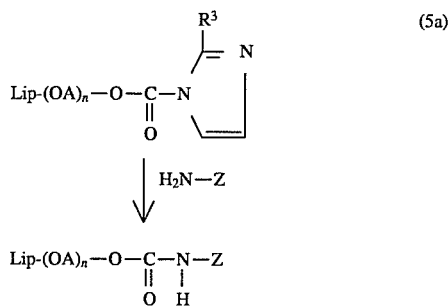

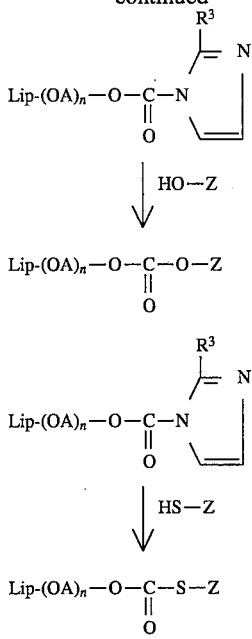

The reactive vesicle according to the present invention, after having been subjected to the fixation reaction, can be purified, if necessary, by a known technique, such as gel filtration, ultrafiltration, dialysis, centrifugation or still sedimentation separation.

The reactive liposome and the functional substance-fixed liposome according to the present invention can enclose therein, namely within the aqueous phase inside the liposome cell or within the membrane itself of the liposome, various materials by a known technique, as in conventional cellular liposomes. The material to be enclosed therein may be, for example, labelling compounds, such as pigments, dyestuffs, radioactive labelling compounds, fluorescent compounds and chemiluminescent compounds; external stimulation-responsive compounds, such as light-responsive compounds, pH-responsive compounds, heat-responsive compounds and electrode-susceptible compounds; physiologically active substances, such as proteins, including enzymes and antibodies, sugars, lipids, glycoproteins, glycolipids and hormones; drugs, such as medicaments; and water-soluble high polymeric materials, such as polyacrylamides, polyvinyl alcohols, α-hydro-ω-hydroxy polyoxyethylene and hyaluronic acid.

As the drugs, medicaments which are expected to maintain their concentration in blood for long periods of time or to reveal a target-directing property towards a specific diseased site or living cells may preferably be employed, such as anticancer agents, antibiotics, antiasthma agents and antiviral agents, though there is no limitation therefor. As the anticancer agent, those described in A. Kubo: "Gan Kagakuryoho" (Chemotherapy of Cancer), Nankodo (1985), above all, doxorubicin, adriamycin, cisplatin, mitomycin, bleomycin, 5-fluorouracil, methotrexate, nitrogen mustard and busulfan may be mentioned. Other drugs include medicaments based on peptides, such as α-, β- and γ-interferons of the gene recombination type, interleukins and superoxide dismutases; antibiotics, such as sulfasan, gentamycin and streptomycin; antiprotists, such as meglumine antimonate; antithrombins, such as heparin, low molecular weight heparin, urokinase, thrombomidulin; immnoactivators, such as muramyl peptides; and antiasthmatic agents, such as theophylline.

The material to be taken up can easily be enclosed within the aqueous phase in the liposome by an adequate method, for example, by using an aqueous solution containing the functional substance upon the preparation of the reactive liposome, by treating the reactive liposome or the functional substance-fixed liposome by the pH-gradient method or the osmotic pressure-gradient method, etc. A material having a membrane-forming ability can be enclosed in the liposome by carrying out the liposome formation procedure using this material together with the membrane-forming components, wherein the material is drawn in the membrane of the liposome. The liposome charged with the enclosed material in this manner can then be subjected, if necessary, to purification treatment by, for example, gel filtration, ultrafiltration, dialysis, centrifugation or still sedimentation separation.

The reactive liposome and the functional substance-fixed liposome is superior in that the functional substance captured by the liposome is difficultly removed from the liposome membrane as compared with that composed of polyoxyalkylene derivative of straight chain, since two fatty acid acyl groups of $R^1C(=O)$ and $R^2C(=O)$ are present in the phospholipid derivative represented by the general formula (1) or (2). Therefore, the reactive liposome and the functional substance-fixed liposome according to the present invention are superior in long term storage stability. Moreover, since the reactive liposome and the functional substance-fixed liposome according to the present invention include the (poly)oxyalkylene chains introduced therein, they are expected to have the effect of introduction of the (poly)oxyalkylene chain taught in the prior arts, such as the long term preservation of the concentration in blood, non-immunogenicity and preventive effect against the leaking out of the material enclosed in the liposome. The functional substance-fixed liposome according to the present invention has the functional substance fixed at the top end of the (poly)oxyalkylene chain, so that the functionality intrinsic of the functional substance can be revealed sufficiently without suffering from any hindering action of the (poly)oxyalkylene chain, resulting in a superior specificity of reaction with a specific substance together with superior target-directing performance (accumulative ability).

The drug delivery liposome according to the present invention which is composed of the reactive liposome or of the functional substance-fixed liposome, functions to carry drugs and medicaments enclosed therein to deliver them to the required site. Such a delivery vesicle is difficult to be captured in reticuloendothelial organs, such as liver, so that it permits maintenance of its concentration in blood for a long period of time with a low tendency to coagulation and, thus, an efficient delivery of drug can be attained. A drug delivery liposome having fixed thereon an antibody or an antigen has an excellent target-directing ability due to the high functioning performance of the antigen or antibody attached to the top end of the (poly)oxyalkylene chain and is utilized as a drug carrier for the drug delivery system to deliver the drug or medicament to the target site at a high efficiency.

The reactive liposome and the functional substance-fixed liposome according to the present invention can be utilized for, in addition to the drug carrier, various functional liposomes and carriers therefor, such as, liposomal preparations, testing drugs, diagnostic drugs, sensors, fixed catalysts, bioreactors, elements for bioelectronics and substitutes for microcapsules, if neccesary, with or without enclosing various materials mentioned above. It is also possible to utilize drug-fixed liposome, namely, a liposome containing a drug fixed thereto, as a carrier for a fixed medicament.

When another polymerizable phospholipid derivative is employed as another membrane-forming component together with the reactive phospholipid derivative represented by the general formula (1) in producing the reactive liposomal vesicle, a polymerizable reactive liposomal vesicle can be obtained. For the polymerizable phospholipid, known ones can be employed, for example, 1,2-di(2,4-octadecadienoyl)-glycero- 3-phosphocholine and those which are described in S. Shimano, J. Sunamoto and K. Inoue; "Liposomes", pp 1313–351 (1988), issued from Nankodo. Among them, 1,2-di(2,4-octadecadienoyl)-glycero-3-phosphocholine is preferred.

The polymerizable liposome can easily be subjected to polymerization by, for example, irradiation of UV-rays, γ-rays and electron beams, using a redox initiator or heating in the presence of an azo-initiator, an organic peroxide or ammonium persulfate. The resulting polymerized liposome has a superior stability and, therefore, can be used in the form of aqueous suspension as such or for preparing a pulverous product by, for example, freeze-drying, to serve for a stable application.

For a reactive vesicle other than a liposome, a reactive fatty emulsion may be employed, which is prepared by emulsifying an oily mixture containing a phospholipid derivative represented by the general formula (1), a vegetable oil component, such as soybean oil and safflower oil, and an unmodified phospholipid component (another phospholipid component), such as soybean lecithin and yolk lecithin, in an aqueous emulsion medium together with other optionally employed additives, such as Intralipid (Trademark, Ohtsuka Pharmac. Co.), emulsifying assistants, stabilizers, isotonizing agents, oil-soluble drugs, such as oil-soluble medicaments and oil-soluble physiological substances. In these reactive fatty emulsions, the phospholipid derivative of the general formula (1) and other membrane-forming components are drawn up towards the interface between the oil phase of the oil droplets and the aqueous phase surrounding it and accumulate there to form a vesicle. The content of the phospholipid derivative represented by the general formula (1) in the oil mixture may preferably amount to 0.01–50 mole %, in particular, 0.5–30 mole %.

The reactive fatty emulsion can be prepared by a known method. For example, the reactive phospholipid derivative of the general formula (1), the vegetable oil component and the unmodified phospholipid component are brought together under addition of, if necessary, other additives and the resulting mixture is then subjected to a rough emulsification on, for example, a homomixer with heating and with an addition of water, whereupon the resulting mixture is homogenized into a finished emulsion by, for example, a pressure-jet homogenizer of, such as, the Manton-Gaulin type. By admixing an oil-soluble drug into the starting oil mixture for producing the fatty emulsion, a reactive fatty emulsion containing the drug in the oil droplets can be prepared.

On the so-obtained reactive fatty emulsion, various functional substances, such as those used in the reactive liposomal vesicles, can be easily fixed in the same manner, whereby a functional substance-fixed fatty emulsion of the present invention can be obtained.

The reactive fatty emulsion and the functional substance-fixed fatty emulsion can be used as drug carriers, testing drugs, diagnostic drugs, sensors and fixed catalysts.

As a reactive vesicle other than those described above, reactive micell can be employed which contains the reactive phospholipid derivative represented by the general formula (1), wherein the micell may be composed of only the phospholipid derivative of the general formula (1) or composed of a combination thereof with, for example, other micell-forming components, such as other phospholipids such as lecithin and cholesterols, oil-soluble drugs such as oil-soluble medicament, or oil-soluble physiological active substance. The reactive micell can be produced by introducing the phospholipid derivative of the general formula (1) solely or in a form of a mixture with other micell-forming component(s) into an aqueous phase in an amount sufficient to exceed the micell forming concentration. By admixing an oil-soluble drug with the starting mixture, a reactive micell having contained therein the drug can also be produced. Also, the reactive micells of the present invention can be used for fixing thereon various functional substances in the same manner as in the reactive fatty emulsion, whereby the functional substance-fixed micell according to the present invention is obtained, which can be used, for example, as carrier for medicaments, testing drugs, diagnostic drugs, sensors and fixed catalyst, similarly to the liposome.

As detailed above, the reactive vesicle according to the present invention contains the reactive phospholipid derivative represented by the general formula (1) as a vesicle-forming component and, thus, can afford to introduce (poly)oxyalkylene chains into the vesicle and to fix on the top ends of these (poly)oxyalkylene chains a larger amount of various functional substances by a covalent bond easily and efficiently through an intermediary by a spacer consisting of the (poly)oxyalkylene chain. The reactive vesicle according to the present invention is superior in long term storage stability.

The functional substance-fixed vesicle according to the present invention contains the phospholipid derivative of the general formula (2) as the vesicle-forming component and, thus, can form a structure in which the functional substance is fixed on the surface of the vesicle through an intermediary by a spacer consisting of the (poly)oxyalkylene chain, so that the functional substance fixed thereon can reveal its functionality sufficiently with superior long term storage stability, while maintaining the concentration of the functional substance in blood for a long period of time.

The drug delivery vesicle according to the present invention is superior in long term stability and can maintain the concentration of the drug in blood for a long time, since it comprises the aforesaid reactive vesicle or the functional substance-fixed vesicle. In the case of the drug delivery vesicle containing an antibody or an antigen fixed thereon, it permits the delivery of various drugs and medicaments to the target site efficiently, due to its superior target-directing ability.

PREFERRED EMBODIMENT OF THE INVENTION

Below, the present invention will further be described by way of specific examples, while these Examples should not be understood as limiting the present invention.

Synthesis Example 1

1.0 g (0.3 mmol) of an α-hydro-ω-carboxyl polyoxyethylene (MW=about 3,000, average addition mole number= about 65) and 68 mg (0.3 mmol) of N,N'-dicyclohexylcarbodiimide were dissolved in 10 ml of ethyl acetate and the solution was stirred at 5° C. for 1 hour. Thereto was then added 10 ml of an ethyl acetate solution containing dissolved therein 217 mg (0.3 mmol) of dipalmitoyl-glycero-phosphoethanolamine and the mixture was stirred for a further 6 hours and the mixture then allowed to stand overnight at 0° C., whereupon the deposited matter was removed by filtration. Then, 49 mg (0.3 mmol) of N,N'-carbonyldiimidazole were added to the filtrate and the

EXAMPLE 1-2

The procedures of Example 1-1 were followed with the exception that a reactive phospholipid derivative of the following formula (7)

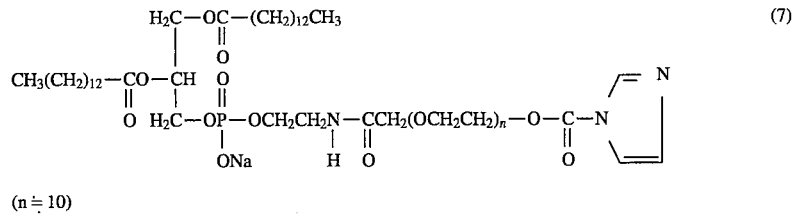

mixture was stirred for 1 hour at room temperature, whereupon the resulting reaction mixture was poured into 100 ml of hexane and the precipitate was separated by filtration to obtain the contemplated reactive phospholipid derivative of the formula (6) given below, as a white powdery product (yield=88%). The progress of the reaction was monitored by IR spectrum (KBr method) by detecting the disappearance of the remaining amino groups in the phosphatidylethanolamine ($N^+H_2$-stretching; 3,000 cm$^{-1}$) and the formation of amide bonds (C=O-stretching; 1,647 cm$^1$) for the intermediate product, on the one hand, and detecting the disappearance of the terminal hydroxyl groups in the polyoxyethylene derivative (OH-stretching; 3,428 cm$^{-1}$) and the formation of the oxycarbonylimidazole bonds (C=O-stretching; 1,760 cm$^{-1}$) for the target product, on the other hand.

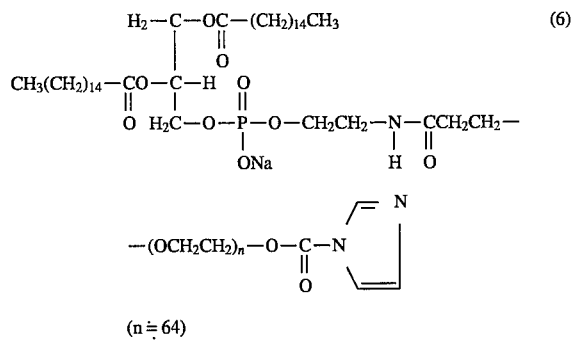

EXAMPLE 1-1

20 mg (26 μmol) of yolk phosphatidylcholine and 3.9 mg (10 μmol) of cholesterol were placed in an eggplant type flask together with 10% by weight, based on the above two compounds, (2.4 mg: 0.7 μmol) of a reactive phospholipid derivative obtained in Synthesis Example 1 and the mixture was dissolved in 2 ml of benzene, whereupon the mixture was subjected to freeze drying. Then, 1 ml of physiological saline was added thereto and, by treatment by a bath-type ultrasonication and using a vortex mixer, a mixture of multilayer liposomes was obtained. This mixture was then processed by an extruder by passing it through a series of three polycarbonate membranes of 3.0 μm, 1.0 μm and 0.2 μm successively in this order, whereby a reactive liposome as a large unllamellar vesicle was obtained. By determining the particle size of the resulting reactive liposome with a laser scattering size distribution meter [NICOMP 370HPL (Trademark) of NICOMP], an average particle size of 255 nm (with CV value of 18%) was found.

was used in an amount of 5% by weight (1.0 μmol), whereby a reactive liposome with an average particle size of 278 nm and a CV value of 23% was obtained.

EXAMPLE 1-3

The procedures of Example 1-1 were followed with the exception that a reactive phospholipid derivative of the following formula (8)

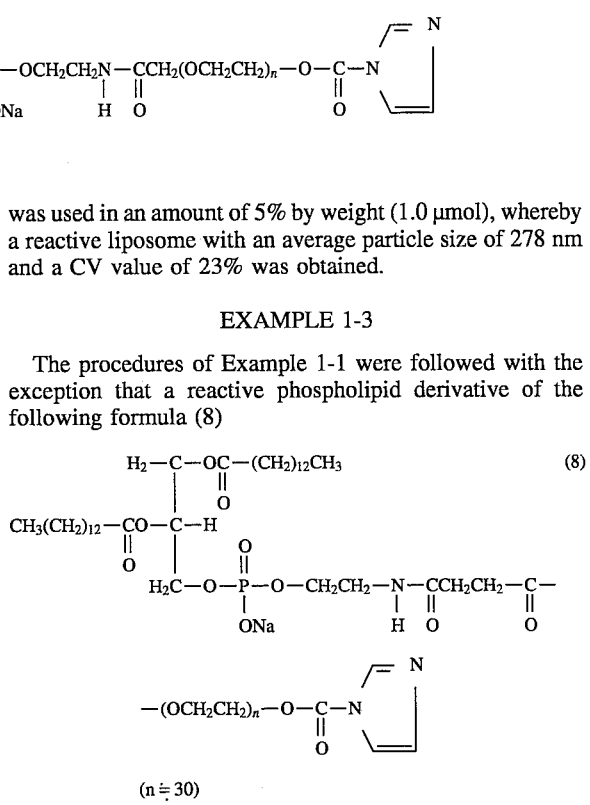

was used in an amount of 30% by weight (3.6 μmol), whereby a reactive liposome with an average particle size of 248 nm and a CV value of 25% was obtained.

EXAMPLE 1-4

The procedures of Example 1-1 were followed with the exception that a reactive phospholipid derivative of the following formula (9)

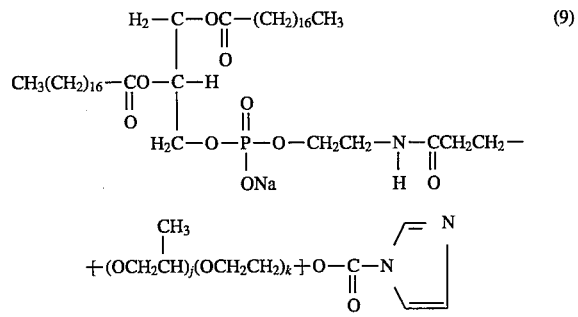

was used in an amount of 1% by weight (0.1 μmol), whereby a reactive liposome with an average particle size of 250 nm and a CV value of 21% was obtained.

EXAMPLE 1-5

The procedures of Example 1-1 were followed with the exception that a reactive phospholipid derivative of the following formula (10)

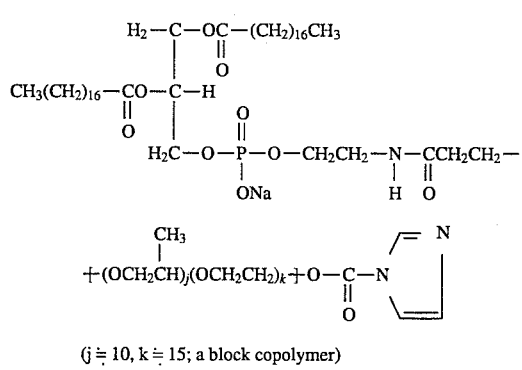

(j ≑ 10, k ≑ 15; a block copolymer)

was used in an amount of 5% by weight (0.6 μmol), whereby a reactive liposome with an average particle size of 250 nm and a CV value of 21% was obtained.

EXAMPLE 1-6

The procedures of Example 1-1 were followed with the exception that a reactive phospholipid derivative of the following formula (11)

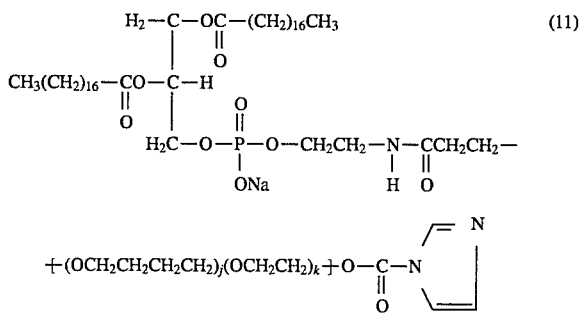

(j ≑ 5, k ≑ 278; a block copolymer)

was used in an amount of 5% by weight (0.1 μmol), whereby a reactive liposome with an average particle size of 291 nm and a CV value of 24% was obtained.

EXAMPLE 1-7

The procedures of Example 1-1 were followed with the exception that a reactive phospholipid derivative of the following formula (12)

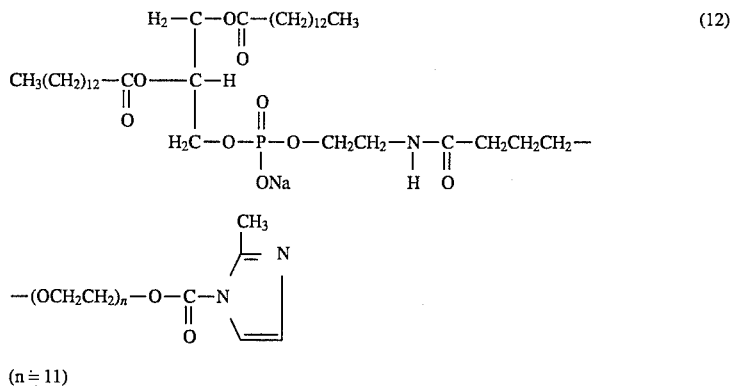

(n ≑ 11)

was used in an amount of 20% by weight (4.0 μmol), whereby a reactive liposome with an average particle size of 221 nm and a CV value of 18% was obtained.

EXAMPLE 1-8

The procedures of Example 1-1 were followed with the exception that the yolk phosphatidylcholine was replaced by 1,2-di(2,4-octadecadienoyl)-glycero-3-phosphocholine (DODPC), whereby a large reactive monolayer liposome with an average particle size of 254 nm (CV value 23%) which exhibited a polymerizability was obtained. By irradiating this liposome with a γ-ray of 0.75 Mrad, the polymerization of DODPC was attained. The polymerized liposome was subjected to gel filtration with Sephadex G-50 and then to freeze drying, whereby a powdery sample was obtained. This liposome powder was able to be regenerated by causing it to swell with physiological saline.

Synthesis Example 2

40 ml of a chloroform solution containing dissolved therein 0.5 g (0.65 mmol) of dipalmitoyl-glycero-phosphocholine and 5 g (1.7 mmol) of an α-hydro-ω-hydroxy polyoxyethylene (MW=ca. 2,000, average addition mole number=about 45) were mixed with 20 ml of 1M acetic acid buffer solution (pH 5.6) containing dissolved therein 40 units of phospholipase D (Toyo Jozo CO., Ltd.) and the mixture was stirred at 40° C. for 12 hours to react them. Then, the reaction mixture was neutralized using 0.1N aqueous solution of sodium hydroxide and the organic phase was concentrated under a reduced pressure. The resulting reaction mixture was subjected to a chromatographic fractionation in silica gel column (20% methanol/chloroform) and the target product was concentrated and dissolved in a small amount of chloroform, from which the target product dipalmitoyl-glycero-phospho polyethylene glycol was obtained by re-precipitation with diethyl ether (yield=30%).

100 mg (0.27 mmol) of the so-obtained dipalmitoylglycero-phospho polyethylene glycol and 87 mg (0.54 mmol) of N,N'-carbonyldiimidazole were introduced into 10 ml of dried chloroform and the mixture was stirred at room temperature for 6 hours. The resulting reaction mixture was subjected to re-precipitation in diethyl ether, whereby the objective reactive phospholipid derivative, a reactive phospholipid derivative of the general formula (1-3) wherein both $R^1C(=O)$ and $R^2C(=O)$ are palmitoyl, $R^3$ is hydrogen, M is sodium, OA is an oxyethylene group and n =ca. 45, was obtained (yield=92%).

The progress of the reaction was monitored by IR spectrum (KBr method) by detecting the disappearance of the terminal hydroxyl groups in the α-hydro-ω-hydroxy polyoxyethylene (OH-stretching; 3,428 $cm^{-1}$) and the formation of the oxycarbonylimidazole bonds (C=O-stretching; 1,760 $cm^{-1}$) for the target product.

EXAMPLE 2-1

20 mg (26 μmol) of yolk phosphatidylcholine and 3.9 mg (10 μmol) of cholesterol were placed in an eggplant type flask together with 10% by weight, based on the above two compounds, (2.4 mg: 0.8 μmol) of a reactive phospholipid derivative obtained in Synthesis Example 2, a reactive phospholipid derivative of the general formula (1-3) in which both $R^1C(=O)$ and $R^2C(=O)$ are a palmitoyl group, $R^3$ denotes a hydrogen atom, M denotes a sodium atom. OA is an oxyethylene group and n represents a number of about 45, and the mixture was dissolved in 2 ml of benzene, whereupon the mixture was subjected to freeze-drying. Then, 1 ml of physiological saline was added thereto and, by treatment by a bath-type ultrasonication and using a vortex mixer, a mixture of multilayer liposomes was obtained. This mixture was then processed by an extruder by passing it through a series of three polycarbonate membranes of 3.0 μm, 1.0 μm and 0.2 μm successively in this order, whereby a reactive liposome as a large unilamellar vesicle was obtained. By determining the particle size of the resulting reactive liposome with a laser scattering size distribution meter [NICOMP 370HPL (Trademark) of NICOMP], an average particle size of 221 nm (with CV value of 19%) was found.

EXAMPLE 2-2

The procedures of Example 2-1 were followed with the exception that 5% by weight (1 μmol) of a reactive phospholipid derivative of the general formula (1-3) in which both $R^1C(=O)$ and $R^2C(=O)$ are a myristoyl group, $R^3$ denotes a hydrogen atom, M denotes a sodium atom, OA is an oxyethylene group and n is a number of about 10 and 5% by weight (0.4 μmol) of dimyristoylglycero-phospho polyethylene glycol (MW=ca. 2,000) were used in place of the reactive phospholipid derivative of Synthesis Example 2, whereby a reactive liposome was obtained (average particle size=268 nm, CV value=22%).

EXAMPLE 2-3

The procedures of Example 2-1 were followed with the exception that 30% by weight (3.5 μmol) of a reactive phospholipid derivative of the general formula (1-3) in which both $R^1C(=O)$ and $R^2C(=O)$ are a myristoyl group, $R^3$ denotes a hydrogen atom, M denotes a sodium atom, OA is an oxyethylene group and n is a number of about 30 were used in place of the reactive phospholipid derivative of Synthesis Example 2, whereby a reactive liposome was obtained (average particle size =238 nm, CV value=22%).

EXAMPLE 2-4

The procedures of Example 2-1 were followed with the exception that 1% by weight (0.1 μmol) of a reactive phospholipid derivative of the general formula (1-3), in which both $R^1C(=O)$ and $R^2C(=O)$ are a stearoyl group, $R^3$ denotes a hydrogen atom, M denotes a sodium atom and the oxyalkylene chain consists of a random addition polymeric chain composed of oxypropylene groups (average addition mole number=ca. 10) and oxyethylene groups (average addition mole number=ca. 25), and 5% by weight (0.4 μmol) of dimyristoylglycero-phospho polyethylene glycol (MW=ca. 2,000) were used in place of the reactive phospholipid derivative of Synthesis Example 2, whereby a reactive liposome was obtained (average particle size=239 nm, CV value=25%).

EXAMPLE 2-5

The procedures of Example 2-1 were followed with the exception that 5% by weight (0.6 μmol) of a reactive phospholipid derivative of the general formula (1-3) in which both $R^1C(=O)$ and $R^2C(=O)$ are a stearoyl group, $R^3$ denotes a hydrogen atom, M denotes a sodium atom and the oxyalkylene chain consists of a block-addition polymeric chain composed of a polyoxypropylene block (average addition mole number=ca. 10) and a polyoxyethylene block (average addition mole number=ca. 15) were used in place of the reactive phospholipid derivative of Synthesis Example 2, whereby a reactive liposome was obtained (average particle size=247 nm, CV value=19%).

EXAMPLE 2-6

The procedures of Example 2-1 were followed with the exception that 5% by weight (0.1 μmol) of a reactive phospholipid derivative of the general formula (1-3) in which both $R^1C(=O)$ and $R^2C(=O)$ are a stearoyl group, $R^3$ denotes a hydrogen atom, M denotes a sodium atom and the oxyalkylene chain consists of a block-addition polymeric chain composed of a polyoxytetramethylene block (average addition mole number=5) and a polyoxyethylene block (average addition mole number=ca. 278) were used in place of the reactive phospholipid derivative of Synthesis Example 2, whereby a reactive liposome was obtained (average particle size=290 nm, CV value=23%).

EXAMPLE 2-7

The procedures of Example 2-1 were followed with the exception that 20% by weight (4.2 μmol) of a reactive phospholipid derivative of the general formula (1-3) in which both $R^1C(=O)$ and $R^2C(=O)$ are a myristoyl group, $R^3$ is methyl, M is sodium atom, OA is an oxyethylene group and n is a number of about 10 were used in place of the reactive phospholipid derivative of Synthesis Example 2, whereby a reactive liposome was obtained (average particle size=211 nm, CV value=19%).

EXAMPLE 2-8

The procedures of Example 2-1 were followed with the exception that the yolk phosphatidylcholine was replaced by 1,2-di(2,4-octadecadienoyl)-glycero- 3-phosphocholine (DODPC), whereby a reactive liposome as a large unilamellar vesicle with an average particle size of 254 nm (CV value 23%) which exhibited a polymerizability was obtained. By irradiating this liposome with a γ-ray of 0.75 Mrad, the polymerization of DODPC was attained. The polymerized liposome was subjected to gel filtration with Sephadex G-50 and then to freeze-drying, whereby a powdery sample was obtained. This liposome powder was able to be regenerated by causing it to swell with physiological saline.

EXAMPLE 3-1

0.5 ml of the reactive liposome solution (solid matter content 2.5% by weight) obtained in Example 1-1 was stirred together with a 0.1M phosphate buffer (pH 7.5) containing 1 mg/ml of horseradish-peroxidase (abbreviated as HRP) at 4° C. for 24 hours, whereby HRP was fixed onto the reactive liposome. This was processed by gel filtration with Sephadex G-50 to collect the liposome-containing fraction. 0.1 ml of a solution (10 mmol/l) of 1,2-phenylenediamine, which is a substrate for HRP, was added to the so-collected fraction and the mixture was incubated at 30° C. for 10 minutes. By adding to this 10 μl of 0.1N sulfuric acid, a coloration into brown was observed.

By this, it was confirmed that HRP can be fixed on the reactive liposome of Example 1-1 simply by being stirred together with it.

EXAMPLE 4-1

0.5 ml of the reactive liposome solution (solid matter content 2.5% by weight) obtained in Example 2-1 was stirred together with a 0.1M phosphate buffer (pH 7.5) containing 1 mg/ml of HRP at 4° C. for 24 hours, whereby HRP was fixed on the reactive liposome. This HRP-fixed liposome was processed by gel filtration with Sephadex G-50 to collect the liposome-containing fraction. 0.1 ml of a solution (10 mmol/l) of 1,2-phenylenediamine, which is a substrate for HRP, was added to the so-collected fraction and the mixture was incubated at 30° C. for 10 minutes. By adding to this 10 μl of 0.1N sulfuric acid, a brown coloration was observed.

From this, it was confirmed that HRP can be fixed on the reactive liposome of Example 2-1 simply by stirring them together.

Comparative Example 1

The procedures of Example 1-1 were followed with the use of only the yolk phosphatidylcholine and the cholestrol in amounts of 20 mg (26 μmol) and 3.9 mg (10 μmol) respectively, whereby a large unilamellar liposome with 2.5 wt. % solid was obtained. When this liposome was processed by reacting HRP thereto in the same manner as in Example 3-1, purifying by gel filtration, adding thereto 0.1 ml of a solution (10 mmol/l) of 1,2-phenylenediamine and incubating the mixture at 30° C. for 10 minutes, followed by addition of 10 μl of 0.1N sulfuric acid, no coloration was found.

From this, it was shown that the liposome of this Comparative Example 1 without containing the reactive phospholipid derivative was not able to fix HRP thereon.

Synthesis Example 3

40 ml of a chloroform solution containing dissolved therein 0.5 g (0.68 mmol) of dipalmitoyl-glycero-phosphocholine and 5 g (2.5 mmol) of an α-hydro-ω-hydroxy polyoxyethylene (MW=ca. 2,000, average addition mole number=about 46) were mixed with 20 ml of 1M acetic acid buffer solution (pH 5.6) containing dissolved therein 40 units of phospholipase D (Asahi Chemical Ind. CO., Ltd.) and the mixture was stirred at 40° C. for 12 hours to react them. Then, the reaction mixture was neutralized using a 0.1N aqueous solution of sodium hydroxide and the organic phase was concentrated under a reduced pressure. The resulting reaction mixture was subjected to chromatographic fractionation in a silica gel column (20% methanol/chloroform) and the target product was concentrated and dissolved in a small amount of chloroform, from which the target product dipalmitoyl-glycero-phospho polyethylene glycol was obtained by re-precipitation with hexane (yield=30%).

100 mg (0.37 mmol) of the so-obtained dipalmitoyl-glycero-phospho polyethylene glycol and 64 mg (0.4 mmol) of N,N'-carbonyldiimidazole were introduced in 10 ml of chloroform and the mixture was stirred at room temperature for 1 hour. The resulting reaction mixture was subjected to re-precipitation in hexane and then to ultrafiltration (fractional molecular weight=500), followed by freeze-drying, whereby a reactive phospholipid derivative of the following formula (13) was obtained.

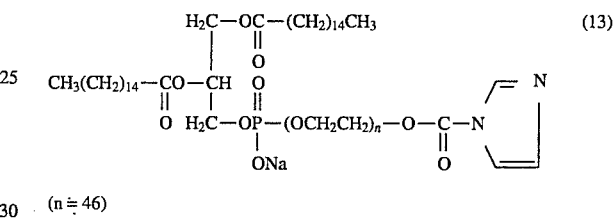

(n ≈ 46)

EXAMPLE 5-1

A phospholipid mixture containing 2 mg (2.6 μmol) of yolk phosphatidylcholine, 1 mg (2.6 μmol ) of cholesterol and 840 μg (6 mole % of the foregoing two) was dissolved in 600 μl of isopropyl ether/chloroform (1:1 v/v). To this solution was added 300 μl of 0.05M borate buffer (pH 9.0). This solution was ultrasonificated for 1 minute to convert it into a W/O emulsion, whereupon the emulsion was heated at 60° C. to evaporate the organic solvent off gradually. This was then passed through a polycarbonate membrane of 0.2 μm to attain a uniform particle size, whereby a large unilamellar vesicle was obtained.

In this liposome, an anticancer agent doxorubicin (abbreviated below as DXR) was enclosed by the pH-gradient method. Namely, 1 mg of DXR was dissolved in the suspension of the above-mentioned liposome and the suspension was adjusted to pH 7.8 with sodium hydroxide, whereupon the resulting suspension was incubated at 60° C. for 10 minutes. Then, the suspension was processed by a gel filtration using Sephadex G-50 to collect the liposome-containing fraction, whereby a DXR-charged liposome was obtained.

To the resulting liposome suspension, 500 μg of a monoclonal antibody (abbreviated below sometimes as 34A or as monoclonal antibody 34A) against gp112 present on the surface of the lung endothelial cell of a mouse was added and the mixture was shaken gently at 4° C. for 48 hours, whereupon the mixture was subjected to purification by a gel filtration using Sephadex G-50 to obtain a 34A-fixed DXR-charged liposome. The average particle size of this liposome was determined using a laser scattering size distribution meter [NICOMP 370HPL (Trademark) of NICOMP] to be 175 nm (CV value=16%).

After this liposome was allowed to stand for one month at 5° C., the average particle size was determined again and found to be 179 nm with CV value of 18%, showing thus a superior stability.

Comparative Example 2

2 mg (2.6 μmol) of yolk phosphatidylcholine, 1 mg (2.6 μmol) of cholesterol and 330 μg (0.52 μmol, 10 mole % of the foregoing two) of α-stearyl-ω-hydroxy polyoxyethylene (average addition mole number=ca. 10) were placed in an eggplant type flask and the mixture was dissolved in 2 ml of benzene, whereupon the mixture was subjected to freeze-drying. Then, 1 ml of physiological saline was added thereto and, by treatment by bath-type ultrasonification and using a vortex mixer, a mixture of multilayer liposomes was obtained. This mixture was then processed by an extruder by passing it through a series of three polycarbonate membranes of 3.0 μm, 1.0 μm and 0.2 μm successively in this order, whereby a reactive liposome as a large unilamellar vesicle was obtained.

By determining the particle size of the resulting liposome in the same manner as in Example 5-1, an average particle size of 196 nm (with CV value of 11%) was found. This then was allowed to stand at 5° C. for one week and the average particle size was determined again, giving a value of 288 nm (CV value=65%). Thus, not only the average particle size but also the CV value were largely changed, showing that no stable liposome was present. From this, it is seen that a liposome containing a membrane-forming component of a polyoxyethylene derivative with a hydrophobic part of monoalkyl group exhibits inferior stability.

EXAMPLE 6-1

1) Preparation of Antibody-fixed Liposome

A phospholipid mixture containing 2 mg (2.6 μmol) of yolk phosphatidylcholine, 1 mg (2.6 μmol) of cholesterol and 840 μg (6 mole % of the foregoing two) of the reactive phospholipid derivative obtained in Synthesis Example 3 was dissolved in 600 μl of isopropyl ether/chloroform (1:1 v/v) containing about 30 KBq of $^{67}$Ga-deferoxamine. To this solution was added 300 μl of 0.05M borate buffer solution (pH 9.0). This solution was ultrasonificated for 1 minute to convert it into a W/O emulsion, whereupon this emulsion was heated at 60° C. to evaporate the organic solvent off gradually. The resulting emulsion was passed through a polycarbonate membrane of 0.2 μm to attain a uniform particle size, whereby a large unilamellar liposome modified with a polyethylene glycol (PEG) chain (polyoxyethylene chain) having an oxycarbonylimidazole group at its terminal end was obtained.

To the so-obtained liposome suspension, 500 μg of a monoclonal antibody 34A was added and the mixture was shaken gently at 4° C. for 8 hours, whereupon the mixture was purified by gel filtration using Sephadex G-50 to obtain a liposome product modified by 34A-fixed PEG and labelled by $^{67}$Ga (averge particle size 184 nm, CV value 15%).

2) Evaluation of Existence Ratio in Organs of Mouse after 1 Hour from Intravenous Injection of 34A-Fixed Liposome The 34A-fixed PEG-modified liposome labelled with $^{67}$Ga obtained in above 1) was injected into each of three Balb/c mice (7-weeks' age, male, weight 20–23 g) through the tail vein at a rate of 500 μg/mouse and the mice were slaughtered after 1 hour from the injection. By counting the $^{67}$Ga radioactivity in each organ, the existence ratio in the organ was calculated as the proportion to the total count upon the injection. Results are summarized in Table 1 below.

Comparative Example 3-1

Using a phospholipid mixture containing 2 mg (2.6 μmol) of yolk phosphatidylcholine, 1 mg (2.6 μmol) of cholesterol and 840 μg (6 mole % of the foregoing two) of the reactive phospholipid derivative obtained in Synthesis Example 3, the procedures of Example 6-1 were followed until the stage of passing through the polycarbonate membrane, whereby a PEG-modified liposome labelled with $^{67}$Ga was obtained (average particle size 188 nm, CV value 15%). Using this liposome, the existence ratio of the radioactivity in the organs of a mouse was observed. Results are summarized also in Table 1 below.

Comparative Example 3-2

A phospholipid mixture containing 2 mg (2.6 μmol) of yolk phosphatidylcholine, 1 mg (2.6 μmol) of cholesterol and 230 μg (6 mole % of the foregoing two) of N-glutaryl-distearylethanolamine was dissolved in 600 μl of isopropylether/chloroform (1:1 v/v) containing about 30 KBq of $^{67}$Ga-deferoxamine. To this solution was added 300 μl of a 10 mM 2-(N-morpholino)ethanesulfonate buffer solution (pH 5.5) containing 150 mM of sodium chloride. This solution was ultrasonificated for 1 minute to convert it into a W/O emulsion, whereupon this emulsion was heated at 60° C. to evaporate the organic solvent off gradually. The resulting emulsion was passed through a polycarbonate membrane of 0.2 μm to attain a uniform particle size, whereby a $^{67}$Ga-labelled liposome was obtained.

To the so-obtained liposome suspension, 58 μl of 0.25M 1-ethyl-3-(3-dimethylaminopropyl)carbodiimide hydrochloride and 58 μl of 0.1M N-hydroxysuccinimide were added and the mixture was shaken gently at room temperature for 10 minutes, whereby a liposome comprising a polyoxyalkylene (PEG) chain having at its terminal end an active ester group was obtained. This was then adjusted using 50 μl of 1M phosphate buffer solution (pH 7.5) and 1N aqueous sodium hydroxide to pH 7.5, whereto 500 μg of the monoclonal antibody 34A against gp112 existing on the surface of the lung endothelial cell of a mouse and the mixture was shaken gently at 4° C. for 8 hours and subjected to purification by gel filtration using Sephadex G-50, whereby a 34A-fixed liposome labelled with $^{67}$Ga was obtained (average particle size 188 nm, CV value 23%). Using this liposome, the existence ratio in the organs of a mouse was observed in the same manner as in Example 6-1. The results are summarized in Table 1 below.

Comparative Example 3-3

Using a phospholipid mixture containing 2 mg (2.6 μmol) of yolk phosphatidylcholine and 1 mg (2.6 μmol) of cholesterol only, the procedures of Example 6-1 were followed until the stage of passing through the polycarbonate membrane, whereby a $^{67}$Ga-labelled liposome was obtained. Using this liposome, the existence ratio of the liposome in organs of a mouse was observed as in Comparative Example 3-2. Results are summarized also in Table 1 below.

TABLE 1

| Organ | Example 6-1 | Compar. Examp. 3-1 | Compar. Examp. 3-2 | Compar. Examp. 3-3 |
|---|---|---|---|---|
| Lung | 52.70 ± 1.7 | 0.7 ± 0.11 | 16.03 ± 0.1 | 1.15 ± 0.01 |
| Blood | 5.00 ± 0.5 | 59.00 ± 10.0 | 5.9 ± 0.5 | 24.8 ± 0.7 |
| Liver | 16.10 ± 0.7 | 17.00 ± 0.9 | 48.1 ± 2.8 | 40.4 ± 1.6 |
| Kidney | 1.76 ± 0.2 | 2.80 ± 0.3 | 1 ± 0.2 | 3.9 ± 0.05 |
| Spleen | 3.90 ± 0.3 | 4.73 ± 0.27 | 7.26 ± 0.7 | 2 ± 0.6 |
| Heart | 0.57 ± 0.07 | 1.20 ± 0.10 | 0 ± 0 | 0.5 ± 0.1 |

Note: The values are each an average of 3 mice±standard error

From the above, it was shown that the liposome product of Example 6-1 having fixed thereon antibody 34A reactive specifically to lung endothelial cell had a superior accumulatability (target-directing ability) in the lung as compared with the PEG-modified liposome product of Comparative Example 3-1, the liposome product of Comparative Example 3-2 having fixed thereon 34A without PEG chain and the conventional liposome product of Comparative Example 3-3. The liposome product of Example 6-1 showed a lower existence ratio in blood than that of the Comparative Examples of 3-1 etc., which may be due to the accumulation in lung and do not indicate that the concentration is not maintained in blood.

We claim:

1. A liposome comprising, as a liposome-forming component, one or more phospholipid derivatives represented by the general formula (1):

$$\begin{array}{c} H_2C-OC-R^1 \\ \phantom{H_2C-O}\| \\ \phantom{H_2C-OC}O \\ R^2-CO-CH \\ \phantom{R^2-}\| \phantom{-CO}\| \\ \phantom{R^2-}O \phantom{-CO}\| \\ \phantom{R^2-CO-}H_2C-OP-(X)_p-(OA)_n-O-C-N\diagup\!\!\!\!=\!\!N \\ \phantom{R^2-CO-H_2C-O}| \phantom{-(X)_p-(OA)_n-O-}\| \phantom{N}\diagdown\!\!\!\!\!-\!\!\!\diagup \\ \phantom{R^2-CO-H_2C-O}OM \phantom{-(X)_p-(OA)_n-O-}O \end{array} \quad (1)$$

in which $R^1C(=O)$ and $R^2C(=O)$ each represent an aliphatic acyl group having 3–30 carbon atoms and may be identical or different from each other, $R^3$ denotes a hydrogen atom or a methyl group, OA represents an oxyalkylene group of 2–4 carbon atoms, n indicates the average addition mole number of added oxyalkylene groups and is a positive number of 1–1,000, with the proviso that the oxyalkylene groups may be identical or different from each other and may be added randomly or in a block when n is 2 or higher, p is 0 or 1, X represents the group $$-OCH_2CH_2N-C(CH_2)_q- \quad \text{or} \quad -OCH_2CH_2N-C(CH_2)_r-C-$$
$$\phantom{-OCH_2CH_2}|\phantom{N-}\| \phantom{C(CH_2)_q-} \phantom{\text{or}} \phantom{-OCH_2CH_2}|\phantom{N-}\|\phantom{C(CH_2)_r-}\|$$
$$\phantom{-OCH_2CH_2}H\phantom{N-}O \phantom{C(CH_2)_q-} \phantom{\text{or}} \phantom{-OCH_2CH_2}H\phantom{N-}O\phantom{C(CH_2)_r-}O$$

wherein q is an integer of 0 to 4 and r is an integer of 1 to 4 and

M denotes a hydrogen atom or an alkali metal atom.

2. A liposome as claimed in claim 1, which contains a drug within the liposome.

3. A liposome having at least one member selected from the group consisting of an amino group, a hydroxyl group and a thiol group attached to a membrane thereof through an urethane bond, a carbonate bond or a thiocarbonate bond, said liposome additionally comprising, as a vesicle-forming component, one or more phospholipid derivatives represented by the general formula (2):

$$\begin{array}{c} H_2C-OC-R^1 \\ \phantom{H_2C-O}\| \\ \phantom{H_2C-OC}O \\ R^2-CO-CH \phantom{O} \\ \phantom{R^2-}\| \phantom{-CO-}\| \\ \phantom{R^2-}O \phantom{-CO-H}H_2C-OP-(X)_p-(OA)_n-O-C-Y \\ \phantom{R^2-CO-H_2C-O}| \phantom{-(X)_p-(OA)_n-O-}\| \\ \phantom{R^2-CO-H_2C-O}OM \phantom{-(X)_p-(OA)_n-O-}O \end{array} \quad (2)$$

in which $R^1C(=O)$ and $R^2C(=O)$ each represent an aliphatic acyl group having 3–30 carbon atoms and may be identical or different from each other, OA represents an oxyalkylene group of 2–4 carbon atoms, n indicates the average additional mole number of added oxyalkylene groups and is a positive number of 1–1,000, with the proviso that the oxyalkylene groups may be identical or different from each other and may be added randomly or in a block when n is 2 or higher, p is 0 or 1, X represents the group $$-OCH_2CH_2N-C(CH_2)_q- \quad \text{or}$$
$$\phantom{-OCH_2CH_2}|\phantom{N-}\|$$
$$\phantom{-OCH_2CH_2}H\phantom{N-}O$$

$$-OCH_2CH_2N-C(CH_2)_r-C-$$
$$\phantom{-OCH_2CH_2}|\phantom{N-}\|\phantom{C(CH_2)_r-}\|$$
$$\phantom{-OCH_2CH_2}H\phantom{N-}O\phantom{C(CH_2)_r-}O$$

wherein q is an integer of 0 to 4 and r is an integer of 1 to 4,

M denotes a hydrogen atom or an alkali metal atom and

Y denotes a residue of a substance.

4. A liposome as claimed in claim 3, which contains a drug.

5. A liposome as claimed in claim 3, wherein the substance is an antibody or an antigen.

6. A liposome as claimed in claim 5, which contains a drug.

7. A drug delivery liposome, comprising a liposome composed of liposome-forming components containing one or more reactive phospholipid derivatives represented by the general formula (1) given below and a drug contained within the liposome:

$$\begin{array}{c} H_2C-OC-R^1 \\ \phantom{H_2C-O}\| \\ \phantom{H_2C-OC}O \\ R^2-CO-CH \phantom{O} \\ \phantom{R^2-}\| \phantom{-CO-}\| \\ \phantom{R^2-}O \phantom{-CO-H}H_2C-OP-(X)_p-(OA)_n-O-C-N\diagup\!\!\!\!=\!\!N \\ \phantom{R^2-CO-H_2C-O}| \phantom{-(X)_p-(OA)_n-O-}\| \phantom{N}\diagdown\!\!\!-\!\!\diagup \\ \phantom{R^2-CO-H_2C-O}OM \phantom{-(X)_p-(OA)_n-O-}O \end{array} \quad (1)$$

in which $R^1C(=O)$ and $R^2C(=O)$ each represent an aliphatic acyl group having 3–30 carbon atoms and may be identical or different from each other, $R^3$ denotes a hydrogen atom or a methyl group, OA represents an oxyalkylene group of 2–4 carbon atoms, n indicates the average addition mole number of added oxyalkylene groups and is a positive number of 1–1,000, with the proviso that the oxyalkylene groups may be identical or different from each other and may be added randomly or in a block when n is 2 or higher, p is 0 or 1, X represents the group

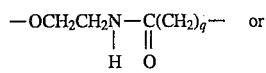

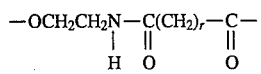

wherein q is an integer of 0 to 4 and r is an integer of 1 to 4 and

M denotes a hydrogen atom or an alkali metal atom.

8. A drug delivery liposome comprising a liposome composed of liposome-forming components containing one or more phospholipid derivatives represented by the general formula (2) given below and a drug contained within the liposome:

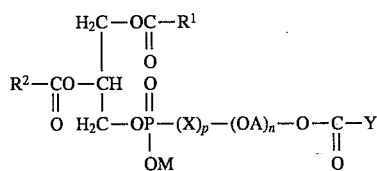

in which $R^1C(=O)$ and $R^2C(=O)$ each represent an aliphatic acyl group having 3–30 carbon atoms and may be identical or different from each other, OA represents an oxyalkylene group of 2–4 carbon atoms, n indicates the average additional mole number of added oxyalkylene groups and is a positive number of 1–1,000, with the proviso that the oxyalkylene groups may be identical or different from each other and may be added randomly or in a block when n is 2 or higher, p is 0 or 1, X represents the group

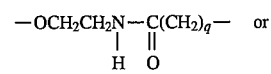

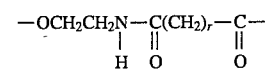

wherein q is an integer of 0 to 4 and r is an integer of 1 to 4,

M denotes a hydrogen atom or an alkali metal atom and

Y denotes a residue of a substance.

9. A liposome as claimed in claim 5, wherein the functional substance is a protein.

10. A drug delivery liposome as claimed in claim 7, wherein the functional substance is an antibody or an antigen.

* * * * *

UNITED STATES PATENT AND TRADEMARK OFFICE
CERTIFICATE OF CORRECTION

PATENT NO. : 5 540 935
DATED : July 30, 1996
INVENTOR(S) : Tsuyoshi MIYAZAKI et al It is certified that error appears in the above-indentified patent and that said Letters Patent is hereby corrected as shown below:

Col. 30, line 22; change "claim 5" to ---claim 3---.

Signed and Sealed this

Third Day of December, 1996

Attest:

BRUCE LEHMAN

Attesting Officer    Commissioner of Patents and Trademarks